United States Patent [19]

Reuschling et al.

[11] Patent Number: 6,046,360
[45] Date of Patent: Apr. 4, 2000

[54] PROCESS FOR PREPARING 4-SUBSTITUTED CIS-CYCLOHEXYLAMINES

[75] Inventors: Dieter Bernd Reuschling, Butzbach; Adolf Heinz Linkies, Frankfurt, both of Germany

[73] Assignee: Hoechst Schering AgrEvo GmbH, Berlin, Germany

[21] Appl. No.: 09/271,042

[22] Filed: Mar. 17, 1999

[30] Foreign Application Priority Data

Mar. 19, 1998 [DE] Germany ............... 198 12 054

[51] Int. Cl.[7] ................................. C07C 209/00
[52] U.S. Cl. ........................... 564/446; 564/307
[58] Field of Search ................... 564/307, 446

[56] References Cited

U.S. PATENT DOCUMENTS 3,994,975  11/1976  Oude Alink et al. ............ 260/563
4,954,654  9/1990   Efner ............................... 564/446
5,395,972  3/1995   Furutani et al. ................. 564/446

FOREIGN PATENT DOCUMENTS

4405728 A1  8/1995  Germany .

OTHER PUBLICATIONS

Academic Press, 1967, pp. 291–303.
Russian Chemical Reviews, 1980, pp. 14–27.
Nippon Kagaku Kaishi, 1989, pp. 641–647.
J. Chem. Res., 1981, pp. 164–165.

*Primary Examiner*—Samuel Barts
*Attorney, Agent, or Firm*—Frommer Lawrence & Haug LLP

[57] ABSTRACT

The present invention relates to a process for preparing 4-substituted cis-cyclohexylamines of high cis-selectivity by reductive amination of cyclohexanones which are substituted in position 4 by an organic radical.

10 Claims, No Drawings

PROCESS FOR PREPARING 4-SUBSTITUTED CIS-CYCLOHEXYLAMINES

The present invention relates to a process for preparing 4-substituted cis-cyclohexylamines of high cis-selectivity by reductive amination of cyclohexanones which are substituted in position 4 by an organic radical.

Reductive aminations of carbonyl compounds are generally carried out by reacting a carbonyl compound and an amine with hydrogen in the presence of a catalyst. Suitable carbonyl compounds are ketones or aldehydes and suitable amines are ammonia, primary and secondary amines. The reductive amination can be carried out at atmospheric pressure or superatmospheric pressure in the presence of nickel or noble metals as catalyst. The reductive amination gives amines which are more highly alkylated than the starting materials. The yields and selectivities that can be obtained depend inter alia on the kind of catalyst and on the properties of the amines and carbonyl compounds employed. Such critical properties are, for example, the steric hindrance or electronic effects of substituents (see, for example: "Reductive alkylation—Preparation of Amines" in *Catalytic Hydrogenation over Platinum Metals*, p. 291–303, Academic Press, New York, 1967 and M. V. Klyuev et al. "Catalytic Amination of Alcohols, Aldehydes, and Ketones" in *Russian Chemical Reviews*, 1980, 49, p. 14–27).

The products of the reductive amination are useful reagents for synthesis.

If 4-substituted cyclohexanones I are reductively aminated using ammonia, the resulting 4-substituted cyclohexylamines are generally obtained as a mixture of the cis-II and trans-isomers III. Undesirable byproducts are, in particular, cyclohexanols IV and bis-cyclohexylamines V.

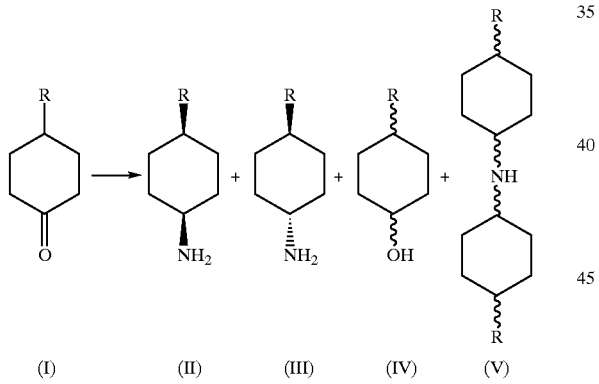

(I)   (II)   (III)   (IV)   (V)

In *Nippon Kagaku Kaishi* 1989, 4, p. 641–647, S. Yada et al. report specifically on the reductive amination of 4-tert-butylcyclohexanone under catalysis by noble metals from the platinum group. With the metals platinum, osmium, iridium, palladium, rhodium and ruthenium that were investigated, the one-step reaction in ethanolic ammonia at 50° C. and a hydrogen pressure of 80 kg/cm$^2$ preferably yields the cis-isomer. The greatest cis-selectivity of 88% (corresponding to a cis-trans ratio of 7.3:1) is obtained here with the expensive noble metal rhodium.

DE-A 44 05 728 discloses the reductive amination of substituted cyclo-hexanones with ammonia and hydrogen in the presence of noble metal borides which, in the case of 4-tert-butylcyclohexanone and palladium boride, leads to the formation of cis-4-tert-butylcyclohexylamine with a maximum cis-selectivity of 89.1% (corresponding to a cis/trans ratio of 8.2:1). A disadvantage of this process consists in the fact that the noble metal borides used here are not commercially available.

A multi-step reaction is described by G. Knupp et al. in *J. Chem. Res. (S)*. 1981, p. 164, where 4-methylcyclohexanone is initially reacted with 1-phenylethylamine to give the corresponding imine. This imine is reduced with hydrogen under Raney-nickel catalysis to give N-(4-methylcyclohexyl)-N-(1-phenylethyl)amine which, after conversion into its hydrochloride, is reduced with hydrogen in the presence of palladium on charcoal, affording the desired 4-methylcyclohexylamine as pure cis-isomer in the form of its hydrochloride with a yield of 83%.

Disadvantages of the prior art processes are the comparatively low cis-selectivity, catalysts which are too cost-intensive to prepare or not commercially available, or too high a number of reaction steps.

It is an object of the present invention to provide a simple process for preparing 4-substituted cyclohexylamines with high cis-selectivity by reductive amination of 4-substituted cyclohexanones which is cost-effective and therefore suitable for industrial use.

This object is achieved by a process for preparing 4-substituted cyclohexylamines of cis configuration by reductive amination of cyclohexanones in the presence of hydrogen and, if appropriate, an organic solvent or a mixture of organic solvents, which process comprises
  a) reacting, in a first step, a cyclohexanone of the formula I with a benzylic amine VI in the presence of a catalyst comprising at least one metal from the group consisting of nickel and the platinum metals, to give N-benzylic cyclohexylamines of the formula VII, and
  b) reacting, in a second step, these N-benzylic cyclohexylamines, if appropriate after the organic solvent has been changed or removed, in the presence of a catalyst comprising at least one metal from the group consisting of the platinum metals, to give the 4-substituted cis-cyclohexylamines of the formula II

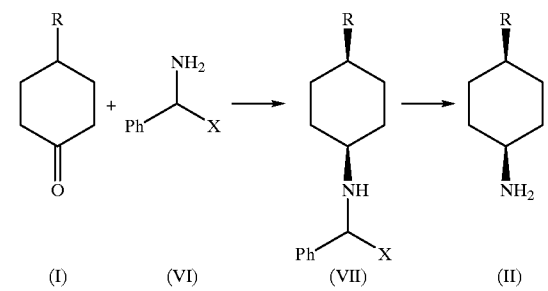

(I)   (VI)   (VII)   (II)

where R, Ph and X are as defined below:
  R is an optionally substituted aliphatic or aromatic radical or a silyl radical which is substituted by alkyl, alkoxy and/or phenyl radicals;
  Ph is phenyl;
  X is hydrogen or methyl.

The process can be carried out both under atmospheric pressure and under superatmospheric pressure in a variety of solvents and in a wide temperature range and leads to the formation of 4-substituted cyclohexylamines with high cis-selectivity.

Suitable catalysts for the first step are those commercially available catalysts which comprise at least one metal from the group consisting of nickel and the platinum metals, preferably nickel, platinum and palladium, particularly preferably platinum and nickel. As usual, these catalysts can be employed in the form of the pure metals or else on suitable support materials, such as activated carbon, alumina, siliceous earth or zeolites. Platinum metals are the metals of the platinum group, i.e. ruthenium, rhodium, palladium, osmium, iridium and platinum. Nickel is usually employed in the form of Raney nickel which is commercially available or can be prepared by known methods (see: Organikum, p. 804, VEB Deutscher Verlag der Wissenschaften, Berlin, 1977). Suitable catalysts for the second step are commercially available catalysts which comprise a metal from the group of the platinum metals, preferably platinum and palladium, particularly preferably palladium.

The reactions of both steps of the process are generally carried out in an organic solvent from the group consisting of the lower aliphatic alcohols, alkylene glycols, lower (cyclo)aliphatic ethers and lower aliphatic carboxylic acids, or in a mixture of two or three of these solvents. Preferred solvents are methanol, ethanol, propanol, n-butanol, ethylene glycol, 1,2-propylene glycol, 1,3-propylene glycol, diisopropyl ether, tert-butyl methyl ether, tetrahydrofuran, formic acid, acetic acid and propionic acid. Moreover, the reaction of the second step can also be carried out in a solvent from the group consisting of the cycloaliphatic hydrocarbons, for example cyclohexane, aromatic hydrocarbons, for example toluene, xylene, cymene or fractions of higher-boiling aromatic hydrocarbons, in a mixture of two or three of the abovementioned solvents, or else neat, i.e. without solvent. Hereinbelow, the term "solvent" refers to one of the abovementioned solvents or a mixture of these solvents.

The reaction of the first step is usually carried out at a temperature between 20 and 120° C., preferably in a range of from 30° below the boiling point of the solvent up to its boiling point, the boiling point of the lowest-boiling solvent being chosen as reference in the case of a solvent mixture. The boiling point mentioned refers to the distillation characteristics of the solvent at atmospheric pressure. The reaction of the second step is usually carried out at a temperature between 50 and 180° C., preferably between 90 and 160° C.

The reaction of the first step can be carried out at a pressure which is usually between atmospheric pressure and 200 bar, preferably between atmospheric pressure and 100 bar. The cis/trans ratio can advantageously be increased by lowering the hydrogen partial pressure by adding an inert gas, for example nitrogen. This addition can be carried out in a molar ratio of hydrogen to inert gas from between 1 (corresponding to 100 mol % of hydrogen) and 0.05 (corresponding to 5 mol % of hydrogen), preferably between 1 and 0.2.

The reaction of the second step can be carried out at a pressure which is usually between atmospheric pressure and 10 bar, preferably at atmospheric pressure. Reactions under pressure can be carried out for example in customary autoclaves such as steel autoclaves.

The reaction of the first step is generally carried out by initially charging a reaction mixture comprising a cyclohexanone of the formula I, a benzylic amine of the formula VI, a catalyst and a solvent in a suitable reaction vessel, and subsequently introducing hydrogen or a hydrogen/nitrogen mixture with vigorous stirring at the desired temperature. It is also possible to introduce hydrogen or the hydrogen/nitrogen mixture into the reaction mixture and to heat this reaction mixture subsequently to the desired temperature. The reaction mixture is then expediently stirred at the desired temperature and with further introduction of hydrogen or hydrogen/nitrogen mixture until, by repeated sample-taking, no more of the benzylic amine, which can be detected easily, for example by thin layer chromatography, can be detected. After the first step, which is preferably carried out until the reaction has gone to completion, has ended, the resulting crude intermediate which comprises a benzylic cyclohexylamine of the formula VII can either a) directly, i.e. without any further work-up, or b) after removal of the catalyst, or c) after evaporation of the solvent, or d) after removal of unwanted minor amounts of the trans-isomer of the benzylic cyclohexylamine, for example by chromatographic separation methods, or e) after an advantageous combination of two or three of the purification steps b), c) and d) has been carried out, be employed for the reaction of the second step.

The reaction of the second step is generally carried out by initially charging a reaction mixture comprising a benzylic cyclohexylamine of the formula VII obtainable by the first step of the process, a catalyst and, if appropriate, a solvent in a suitable reaction vessel, and subsequently introducing hydrogen at the desired temperature. It is also possible to introduce hydrogen into the reaction mixture and to heat this reaction mixture subsequently to the desired temperature. The reaction mixture is then expediently stirred at the desired temperature and with further introduction of hydrogen until, by repeated sample-taking, no more of the benzylic cyclohexylamine, which can be detected easily, for example by thin layer chromatography, can be detected. The second step of the process is preferably carried out until the reaction has gone to completion. The reaction products of the second step, the 4-substituted cyclohexylamines of cis configuration of the formula II, are generally obtained in very high purity and can be isolated by simply removing the catalyst, for example by filtration, and, if appropriate, by evaporation of the solvent. If required, the crude reaction products of the second step can be purified by customary purification methods, such as recrystallization and/or chromatographic methods.

An optionally substituted aliphatic radical is an acyclic aliphatic radical which may be branched or straight-chain and which is unsubstituted, interrupted by 2 or 3 oxygen atoms or substituted by halogen, alkoxy, haloalkoxy, alkoxycarbonyl. It can also be a cycloaliphatic radical which is unsubstituted or substituted by halogen, alkoxy, haloalkoxy, alkoxycarbonyl. An optionally substituted aromatic radical is unsubstituted phenyl, naphthyl, phenylalkyl, or phenyl, naphthyl or phenylalkyl which is substituted by one or more identical or different radicals from the group consisting of halogen, hydroxyl, alkyl, alkoxy, haloalkyl, haloalkoxy, cyano, carboxyl and alkoxycarbonyl.

Preferred meanings of R are $(C_2-C_8)$-alkyl, $(C_3-C_8)$-cycloalkyl, halo-$(C_2-C_8)$-alkyl, halo-$(C_3-C_8)$-cycloalkyl, $(C_1-C_4)$-alkoxy-$(C_1-C_6)$-alkyl, halo-$(C_1-C_4)$-alkoxy-$(C_1-C_6)$-alkyl, halo-$(C_1-C_4)$-alkoxy-halo-$(C_1-C_6)$-alkyl, $(C_3-C_8)$-alkyl which is interrupted by 2 or 3 oxygen atoms, $(C_1-C_6)$-alkoxycarbonyl, $(C_1-C_6)$-alkoxycarbonyl-$(C_1-C_6)$-alkyl, tri-$(C_1-C_6)$-alkylsilyl, di-$(C_1-C_6)$-alkyl-$(C_3-C_6)$-cycloalkylsilyl, $(C_1-C_4)$-alkoxy-di-$(C_1-C_6)$-alkylsilyl, di-$(C_1-C_4)$-alkoxy-$(C_1-C_6)$-alkylsilyl, di-$(C_1-C_6)$-alkyl-halo-$(C_1-C_6)$-alkylsilyl, di-$(C_1-C_6)$-alkylphenylsilyl, $(C_1-C_6)$-alkyldiphenylsilyl, phenyl or phenyl-$(C_1-C_6)$-alkyl which is optionally substituted by one or more identical or different radicals from the group consisting of halogen, hydroxyl, $(C_1-C_3)$-alkyl, $(C_1-C_3)$-alkoxy, halo-$(C_1-C_3)$-alkyl, halo-$(C_1-C_3)$-alkoxy, cyano, carboxyl and $(C_1-C_3)$-alkoxycarbonyl.

Particularly preferred meanings of R are $(C_2-C_6)$-alkyl, $(C_3-C_6)$-cycloalkyl, halo-$(C_2-C_6)$-alkyl, halo-$(C_3-C_6)$- cycloalkyl, $(C_1-C_4)$-alkoxy-$(C_1-C_4)$-alkyl, halo-$(C_1-C_4)$-alkoxy-$(C_1-C_4)$-alkyl, $(C_3-C_8)$-alkyl which is interrupted by 2 or 3 oxygen atoms, $(C_1-C_4)$-alkoxycarbonyl, $(C_1-C_4)$-alkoxycarbonyl-$(C_1-C_4)$-alkyl, tri-$(C_1-C_4)$-alkylsilyl, di-$(C_1-C_4)$-alkyl-$(C_3-C_6)$-cycloalkylsilyl, $(C_1-C_4)$-alkoxy-di-$(C_1-C_4)$-alkylsilyl, di-$(C_1-C_4)$-alkoxy-$(C_1-C_4)$-alkylsilyl, di-$(C_1-C_4)$-alkyl-halo-$(C_1-C_4)$-alkylsilyl, di-$(C_1-C_4)$-alkylphenylsilyl, $(C_1-C_4)$-alkyldiphenylsilyl, phenyl or phenyl-$(C_1-C_4)$-alkyl which is optionally substituted by one or two identical or different radicals from the group consisting of halogen, hydroxyl, $(C_1-C_3)$-alkyl, $(C_1-C_3)$-alkoxy, halo-$(C_1-C_3)$-alkyl, halo-$(C_1-C_3)$-alkoxy and cyano.

The abovementioned terms are to be understood as follows: "$(C_2-C_8)$-alkyl" is a straight-chain or branched hydrocarbon radical having two, three, four, five, six, seven or eight carbon atoms, for example ethyl, propyl, 1-methylethyl, butyl, 1-methylpropyl, 2-methylpropyl, 1,1-dimethylethyl, pentyl, 2-methylbutyl, 1,1-dimethylpropyl, hexyl, heptyl, octyl und 1,1,3,3-tetramethylbutyl. "$(C_1-C_4)$-alkyl" is similarly a straight-chain or branched hydrocarbon radical having one, two, three or four carbon atoms, namely methyl, ethyl, propyl, 1-methylethyl, butyl, 1-methylpropyl, 2-methylpropyl, 1,1-dimethylethyl. The other general alkyl definitions are to be understood similarly. "$(C_3-C_8)$-cycloalkyl" is cyclopropyl, cyclobutyl, cyclopentyl, cyclohexyl, cycloheptyl and cyclooctyl. "$(C_1-C_4)$-alkoxy" is an alkoxy group whose hydrocarbon radical may correspondingly have the meaning given under the term "$(C_1-C_4)$-alkyl". The other general terms for alkoxy radicals are to be understood in a similar way.

"Halogen" is to be understood as fluorine, chlorine, bromine or iodine, preferably fluorine or chlorine.

The terms "halo-$(C_2-C_8)$-alkyl", "halo-$(C_3-C_8)$-cycloalkyl" and "halo-$(C_1-C_4)$-alkoxy" and similar terms mean that one or more hydrogen atoms of one or more carbon atoms in these radicals has/have been replaced by a corresponding number of identical or different halogen atoms. In the combined terms—such as, for example, "$(C_1-C_4)$-alkoxy-$(C_1-C_6)$-alkyl"—the radical mentioned first in each case can be attached to any carbon atom of the radical mentioned second.

The 4-cyclohexylamines prepared by this process are used as starting materials in the synthesis of active compounds.

The following examples illustrate the invention.

EXAMPLES

Commercial reagents, solvents and catalysts were employed without any further purification. The catalysts used were:

Pt-C: platinum on activated carbon, 5% (Degussa, Type F10 P/D)

Ra-Ni: Raney nickel (prepared according to 'Organikum')

Pd-C: palladium on activated carbon, 5% (Fluka)

The Raney nickel types B111W and B113W are commercially available from Degussa and were employed in dry form or moistened with methanol.

The cis/trans ratios were determined by HPLC using a column of the type Chiracel OD (eluent n-hexane/2-propanol 90:10, flow rate 1 ml/min, detection wavelength 210.4 nm) or by GF using a Widebore column of the type Carbowax HP 20 (length 30 m, internal diameter 5.3 cm, layer thickness 2.65 μm, thermal-conductivity detector).

Procedure for the first step of the process:

Examples 1a-1l

Reductive Amination of 4-tert-butylcyclohexanone With Benzylamine or 1-phenylethylamine in Pure Hydrogen Equimolar amounts of 4-tert-butylcyclohexanone and benzylamine or 1-phenylethylamine are vigorously stirred in the solvent in question in the presence of a catalyst and in an atmosphere of pure hydrogen. Once no more benzylamine or 1-phenylethylamine can be detected by taking samples, 200 ml of ethyl acetate are added if the solvent used is ethylene glycol. The reaction mixture is washed three times with water, filtered, dried over $MgSO_4$ and concentrated under reduced pressure. If other solvents are used, the reaction mixture is filtered off directly after the reaction has ended, the catalyst is washed with methanol and the filtrate is concentrated under reduced pressure. In each case, the crude product has the cis-selectivity stated in Table 1 (determination by HPLC). Crystallization of the hydrochlorides or purification by column chromatography (silica gel, ethyl acetate) gives pure N-benzyl-cis-4-tert-butyl-cyclohexylamine or pure N-(1-phenylethyl)-cis-4-tert-butyl-cyclohexylamine.

TABLE 1

| No. | Ketone [mmol] | Benzylamine [mmol] | 1-Phenylethylamine [mmol] | Solvent | Catalyst Type/Amount [g] | Temperature [° C.] | Pressure [bar] | cis/trans-Ratio |
|---|---|---|---|---|---|---|---|---|
| 1a | 40 | 40 | — | 100 ml ethylene glycol | Pt—C/0.4 | 25 | — | 11.8:1 |
| 1b | 40 | 40 | — | 60 ml methanol | Ra—Ni/1.4 | 40 | 100 | 19.5:1 |
| 1c | 200 | 200 | — | 250 ml methanol | Ra—Ni/1.8 | 25 | — | 25.0:1 |
| 1d | 20 | 20 | — | 150 ml ethylene glycol | Pd—C/0.4 | 25 | — | 9.0:1 |
| 1e | 20 | — | 20 | 50 ml ethylene glycol | Pt—C/0.4 | 25 | — | 13.9:1 |
| 1f | 20 | — | 20 | 40 ml ethylene glycol + 10 ml methanol | Pt—C/0.4 | 25 | — | 11.0:1 |
| 1g | 60 | 60 | — | 150 ml ethanol | Pt—C/0.4 | 78 | — | 12.5:1 |
| 1h | 60 | 60 | — | 150 ml methanol | Pt—C/0.4 | 65 | — | 15.0:1 |
| 1i | 60 | 60 | — | 150 ml ethyl acetate | Pt—C/0.4 | 77 | — | 9.0:1 |
| 1j | 60 | 60 | — | 150 ml tert-butyl methyl ether | Pt—C/0.4 | 55 | — | 12.0:1 |

TABLE 1-continued

| No. | Ketone [mmol] | Benzylamine [mmol] | 1-Phenylethylamine [mmol] | Solvent | Catalyst Type/Amount [g] | Temperature [° C.] | Pressure [bar] | cis/trans-Ratio |
|---|---|---|---|---|---|---|---|---|
| 1k | 80 | 80 | — | 100 ml methanol | Ra—Ni B113W, 1.0 g, moistened with methanol | 25 | — | 18.5:1 |
| 1l | 80 | 80 | — | 100 ml methanol | Ra—Ni B111W, 1.0 g moistened with methanol | 25 | — | 20:1 |

Examples 2a, 2b

Reductive Amination of 4-tert-butylcyclohexanone With Benzylamine in a Hydrogen/Nitrogen Atmosphere Under atmospheric pressure and at the temperature stated, 9.26 g (60 mmol) of 4-tert-butylcyclohexanone and 6.56 ml (60 mmol) of benzylamine are stirred vigorously in 150 ml of the solvent stated in the presence of 0.4 g of platinum on activated carbon (5%) in a hydrogen/nitrogen atmosphere. Once no more benzylamine can be detected by taking samples, the reaction mixture is filtered off through a filter accelerator, the catalyst is washed with the solvent in question and the filtrate is concentrated under reduced pressure. The cis/trans ratio of the residue is examined by HPLC.

TABLE 2

| No. | Solvent | Temperature [° C.] | $H_2$ (l/h) | $N_2$ (l/h) | Crude yield [%] | cis/trans Ratio |
|---|---|---|---|---|---|---|
| 2a | ethanol | 78 | 60 | 40 | 100.5 | 17.4:1 |
| 2b | methanol | 65 | 60 | 40 | 96.5 | 19.3:1 |

Example 3

Reductive Amination of 4-(1,1,3,3-tetramethyl)-cyclohexanone With Benzylamine in a Atmosphere of Pure Hydrogen and in the Presence of Platinum At atmospheric pressure, 60 mmol (12.6 g) of (4-(1,1,3,3-tetramethyl)-cyclohexanone and 60 mmol (6.5 g) of benzylamine are stirred vigorously in 150 ml of methanol in the presence of 0.4 g of platinum on activated carbon (5%) in a atmosphere of pure hydrogen. Once no more benzylamine can be detected by taking samples, the reaction mixture is filtered through a filter accelerator, the catalyst is washed with methanol and the filtrate is concentrated under reduced pressure. The cis/trans ratio of the residue is examined by HPLC and amounts to 29.3:1.

Example 4

Reductive Amination of 4-methyl-cyclohexanone With Benzylamine in the Presence of Raney Nickel At atmospheric pressure and room temperature, 80 mmol of 4-methyl-cyclohexanone (8.98 g) and 80 mmol (8.74 ml) of benzylamine are stirred vigorously in 100 ml of methanol in the presence of 1–1.5 g of Raney nickel in an atmosphere of hydrogen. Once no more benzylamine can be detected by taking samples, the reaction mixture is filtered through filter accelerators, the catalyst is washed with methanol and the filtrate is concentrated under reduced pressure. The cis/trans ratio of the residue is examined by HPLC and amounts to 7:1.

Procedure for the second step of the process:

Examples 5a,b

Preparation of cis 4-substituted Cyclohexylamines by Catalytic Hydrogenolysis of N-(1-phenylethyl)-cis-4-substituted Cyclohexylamines or N-benzyl-cis-4-substituted Cyclohexylamines

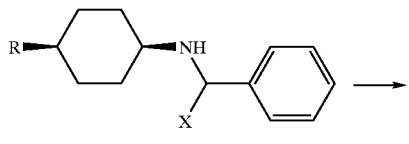

VII

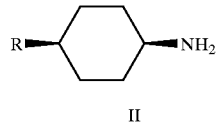

II

Under atmospheric pressure, 200 mmol of an N-(1-phenylethyl)-cis-4-substituted cyclohexylamine or an N-benzyl-cis-4-substituted cyclohexylamine are vigorously stirred with or without solvent in the presence of 0.4 to 1.0 g of palladium on activated carbon (5%) in a hydrogen atmosphere. Once no more starting material can be detected, the crude product is purified by distillation, crystallization or column chromatography.

TABLE 5

| No. | R | X | Solvent [ml] | Temperature [° C.] | Product II [%] |
|---|---|---|---|---|---|
| 5a | $(H_3C)_3C$ | H | — | 100 | 93.6 |
| 5b | $(H_3C)_3C$ | $H_3C$ | — | 100 | 89.6 |

We claim:

1. A process for preparing 4-substituted cyclohexylamines of cis configuration by reductive amination of cyclohexanones in the presence of hydrogen and, if appropriate, an organic solvent or a mixture of organic solvents, which process comprises a) reacting, in a first step, a cyclohexanone of the formula I with a benzylic amine VI in the presence of a catalyst comprising at least one metal from the group consisting of nickel and the platinum metals, to give N-benzylic cyclohexylamines of the formula VII, and b) reacting, in a second step, these N-benzylic cyclohexylamines, if appropriate after the organic solvent has been changed or removed, in the presence of a catalyst comprising at least one metal from the group consisting of the platinum metals, to give the 4-substituted cis-cyclohexylamines of the formula II

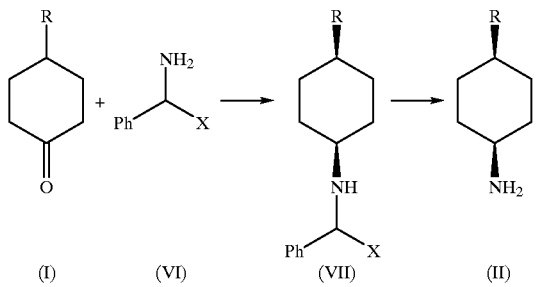

where R, Ph and X are as defined below:
R is an optionally substituted aliphatic or aromatic radical or a silyl radical which is substituted by alkyl, alkoxy and/or phenyl radicals;
Ph is phenyl;
X is hydrogen or methyl.

2. The process as claimed in claim 1, wherein in the first step a nickel-, platinum- or palladium-comprising catalyst and in the second step a platinum- or palladium-comprising catalyst is used.

3. The process as claimed in claim 2, wherein in the first step a nickel- or platinum-comprising catalyst and in the second step a palladium-comprising catalyst is used.

4. The process as claimed in claim 1, wherein 4-substituted cyclohexanones of the formula I are reductively aminated, in which R
  a) is an acyclic aliphatic radical which may be branched or straight-chain and which is optionally interrupted by 2 or 3 oxygen atoms or substituted by one or more identical or different radicals from the group consisting of halogen, alkoxy, haloalkoxy, alkoxycarbonyl, or
  b) is a cycloaliphatic radical which is optionally substituted by one or more identical or different radicals from the group consisting of halogen, alkoxy, haloalkoxy, alkoxycarbonyl, or
  c) is a silyl radical which is substituted by three identical or different radicals from the group consisting of alkyl, alkoxy and phenyl, or
  d) is a phenyl, naphthyl or phenylalkyl which is optionally substituted by one or more identical or different radicals from the group consisting of halogen, hydroxyl, alkyl, alkoxy, haloalkyl, haloalkoxy, cyano, carboxyl and alkoxycarbonyl.

5. The process as claimed in claim 4, wherein 4-substituted cyclohexanones of the formula I are reductively aminated, in which R is $(C_2-C_8)$-alkyl, $(C_3-C_8)$-cycloalkyl, halo-$(C_2-C_8)$-alkyl, halo-$(C_3-C_8)$-cycloalkyl, $(C_1-C_4)$-alkoxy-$(C_1-C_6)$-alkyl, halo-$(C_1-C_4)$-alkoxy-$(C_1-C_6)$-alkyl, halo-$(C_1-C_4)$-alkoxy-halo-$(C_1-C_6)$-alkyl, $(C_3-C_8)$-alkyl which is interrupted by 2 or 3 oxygen atoms, $(C_1-C_6)$-alkoxycarbonyl, $(C_1-C_6)$-alkoxycarbonyl-$(C_1-C_6)$-alkyl, tri-$(C_1-C_6)$-alkylsilyl, di-$(C_1-C_6)$-alkyl-$(C_3-C_6)$-cycloalkylsilyl, $(C_1-C_4)$-alkoxy-di-$(C_1-C_6)$-alkylsilyl, di-$(C_1-C_4)$-alkoxy-$(C_1-C_6)$-alkylsilyl, di-$(C_1-C_6)$-alkyl-halo-$(C_1-C_6)$-alkylsilyl, di-$(C_1-C_6)$-alkylphenylsilyl, $(C_1-C_6)$-alkyldiphenylsilyl, phenyl or phenyl-$(C_1-C_6)$-alkyl which is optionally substituted by one or more identical or different radicals from the group consisting of halogen, hydroxyl, $(C_1-C_3)$-alkyl, $(C_1-C_3)$-alkoxy, halo-$(C_1-C_3)$-alkyl, halo-$(C_1-C_3)$-alkoxy, cyano, carboxyl and $(C_1-C_3)$-alkoxycarbonyl.

6. The process as claimed in claim 5, wherein 4-substituted cyclohexanones of the formula I are reductively aminated, in which R is $(C_2-C_6)$-alkyl, $(C_3-C_6)$-cycloalkyl, halo-$(C_2-C_6)$-alkyl, halo-$(C_3-C_6)$-cycloalkyl, $(C_1-C_4)$-alkoxy-$(C_1-C_4)$-alkyl, halo-$(C_1-C_4)$-alkoxy-$(C_1-C_4)$-alkyl, $(C_3-C_8)$-alkyl which is interrupted by 2 or 3 oxygen atoms, $(C_1-C_4)$-alkoxycarbonyl, $(C_1-C_4)$-alkoxycarbonyl-$(C_1-C_4)$-alkyl, tri-$(C_1-C_4)$-alkylsilyl, di-$(C_1-C_4)$-alkyl-$(C_3-C_6)$-cycloalkylsilyl, $(C_1-C_4)$-alkoxy-di-$(C_1-C_4)$-alkylsilyl, di-$(C_1-C_4)$-alkoxy-$(C_1-C_4)$-alkylsilyl, di-$(C_1-C_4)$-alkyl-halo-$(C_1-C_4)$-alkylsilyl, di-$(C_1-C_4)$-alkylphenylsilyl, $(C_1-C_4)$-alkyldiphenylsilyl, phenyl or phenyl-$(C_1-C_4)$-alkyl which is optionally substituted by one or two identical or different radicals from the group consisting of halogen, hydroxyl, $(C_1-C_3)$-alkyl, $(C_1-C_3)$-alkoxy, halo-$(C_1-C_3)$-alkyl, halo-$(C_1-C_3)$-alkoxy and cyano.

7. The process as claimed in claim 1, wherein the reaction of the first step is carried out in a solvent from the group consisting of the lower aliphatic alcohols, alkylene glycols, lower (cyclo)aliphatic ethers and lower aliphatic carboxylic acids or in a mixture of the abovementioned solvents, and the reaction of the second step is carried out in a solvent from the group consisting of the lower aliphatic alcohols, alkylene glycols, lower (cyclo)aliphatic ethers, lower aliphatic carboxylic acids, aromatic hydrocarbons, cycloaliphatic hydrocarbons or in a mixture of the abovementioned solvents or without solvent.

8. The process as claimed in claim 1, wherein the reaction of the first step is carried out at a pressure between 0 and 100 bar and the reaction of the second step is carried out at a pressure between 0 and 10 bar.

9. The process as claimed in claim 1, wherein the reaction of the first step is carried out in a hydrogen/nitrogen atmosphere in which the proportion of hydrogen is between 100 and 20 mol %.

10. The process as claimed in claim 1, wherein the reaction of the first step is carried out at a temperature of from 30° below the boiling point of the solvent used up to its boiling point, and the reaction of the second step is carried out at a temperature between 90 and 160° C.

* * * * *